(12) United States Patent
Soro et al.

(10) Patent No.: US 9,706,923 B2
(45) Date of Patent: Jul. 18, 2017

(54) SYSTEM AND METHOD FOR ADAPTIVE INTERFERENCE MITIGATION IN WIRELESS SENSOR NETWORK

(71) Applicant: General Electric Company, Schenectady, NY (US)

(72) Inventors: Stanislava Soro, Niskayuna, NY (US); David Michael Davenport, Niskayuna, NY (US); Steven William Wik, Niskayuna, NY (US); S M Shajedul Hasan, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 156 days.

(21) Appl. No.: 14/189,335

(22) Filed: Feb. 25, 2014

(65) Prior Publication Data
US 2015/0238082 A1 Aug. 27, 2015

(51) Int. Cl.
*A61B 5/024* (2006.01)
*A61B 5/021* (2006.01)
(Continued)

(52) U.S. Cl.
CPC ............ *A61B 5/0024* (2013.01); *A61B 5/002* (2013.01); *A61B 5/021* (2013.01);
(Continued)

(58) Field of Classification Search
USPC ....... 455/12.1, 41.2; 600/300, 301; 370/336, 370/296, 252, 328, 337, 311, 503, 217,
(Continued)

(56) References Cited

U.S. PATENT DOCUMENTS 6,047,171 A * 4/2000 Khayrallah .......... H04B 1/1036
455/266
8,199,000 B2   6/2012 Ross et al.
(Continued)

FOREIGN PATENT DOCUMENTS

WO   2011/010755 A1   1/2011

OTHER PUBLICATIONS

Hohn H. Gass, Jr. et al., "An Adaptive-Transmission Protocol for Frequency-Hop Wireless Communication Networks", Wireless Networks, vol. 7, 2001, (pp. 487-495, 9 pages total.
(Continued)

*Primary Examiner* — Edward Urban
*Assistant Examiner* — Ralph H Justus
(74) *Attorney, Agent, or Firm* — Pabitra K. Chakrabarti

(57) ABSTRACT

A system includes wireless sensor devices monitoring a patient, a gateway device providing dual-frequency adaptive protocol time synchronization signals to the sensor devices, the time synchronization signals including a communication frame structure having time slots including two beacon signal time slots and a plurality of data slots, where the sensor devices transmit respective patient data a first time interleaved within a first data slot and a second time interleaved within a second data slot, the first interleaved data transmission and the second interleaved data transmission are each transmitted at respective different frequencies provided to the sensor devices in beacon signals received from the gateway device. The first interleaved data transmission includes both current data and previous data from the at least two wireless sensor devices, and a frequency agility pattern separates adjacent channels by a respective predetermined frequency offset. A method and non-transitory medium are disclosed.

23 Claims, 5 Drawing Sheets

(51) Int. Cl.
*A61B 5/00* (2006.01)
*A61B 5/145* (2006.01)
*A61B 5/0402* (2006.01)
*H04B 1/00* (2006.01)
*G06F 19/00* (2011.01)
*H04J 3/00* (2006.01)
*H04L 1/00* (2006.01)
*H04W 4/00* (2009.01)
*H04L 29/08* (2006.01)

(52) U.S. Cl.
CPC ........ *A61B 5/02405* (2013.01); *A61B 5/0402* (2013.01); *A61B 5/14542* (2013.01); *G06F 19/3418* (2013.01); *H04B 1/00* (2013.01); *H04J 3/00* (2013.01); *H04L 1/00* (2013.01); *H04L 67/12* (2013.01); *H04W 4/006* (2013.01)

(58) Field of Classification Search
USPC ................. 370/329; 340/286.02, 870.01
See application file for complete search history.

(56) References Cited

U.S. PATENT DOCUMENTS

| | | | | |
|---|---|---|---|---|
| 8,301,103 | B2* | 10/2012 | Huang | H03D 1/22 375/324 |
| 8,639,324 | B2 | 1/2014 | Elferri et al. | |
| 2005/0195859 | A1 | 9/2005 | Mahany | |
| 2006/0104301 | A1 | 5/2006 | Beyer et al. | |
| 2006/0280133 | A1* | 12/2006 | Nomura | H04L 12/40136 370/276 |
| 2007/0211681 | A1 | 9/2007 | Sun et al. | |
| 2007/0258508 | A1* | 11/2007 | Werb | H04W 24/02 375/140 |
| 2009/0088605 | A1* | 4/2009 | Ross | A61B 5/0002 600/300 |
| 2009/0168796 | A1 | 7/2009 | Pandey et al. | |
| 2009/0268747 | A1* | 10/2009 | Kurata | H04L 1/1832 370/412 |
| 2010/0034159 | A1* | 2/2010 | Shin | H04W 72/1257 370/329 |
| 2010/0075611 | A1* | 3/2010 | Budampati | H04B 7/0885 455/67.11 |
| 2010/0142425 | A1* | 6/2010 | Lee | H04W 52/146 370/311 |
| 2010/0142435 | A1* | 6/2010 | Kim | H04B 7/2606 370/315 |
| 2010/0249881 | A1* | 9/2010 | Corndorf | A61N 1/37276 607/60 |
| 2011/0004073 | A1 | 1/2011 | Corroy et al. | |
| 2011/0149759 | A1* | 6/2011 | Jollota | A61B 5/0024 370/252 |
| 2011/0201945 | A1 | 8/2011 | Li et al. | |
| 2012/0315942 | A1 | 12/2012 | Lin et al. | |
| 2013/0143501 | A1* | 6/2013 | Huang | H04B 15/00 455/42 |
| 2013/0195083 | A1* | 8/2013 | Kim | H04W 72/0446 370/336 |
| 2013/0265962 | A1* | 10/2013 | Ouchi | H04W 72/02 370/329 |
| 2013/0315085 | A1* | 11/2013 | Krishnamurthy | H04L 5/001 370/252 |
| 2014/0099978 | A1* | 4/2014 | Egner | H04W 4/028 455/456.6 |

OTHER PUBLICATIONS

Dunkels, Adam et al., "An Adaptive Communication Architecture for Wireless Sensor Networks", Proceedings of the 5th International Conference on Embedded Networked Sensor System, 2007, (pp. 335-349, 15 pages total).

* cited by examiner

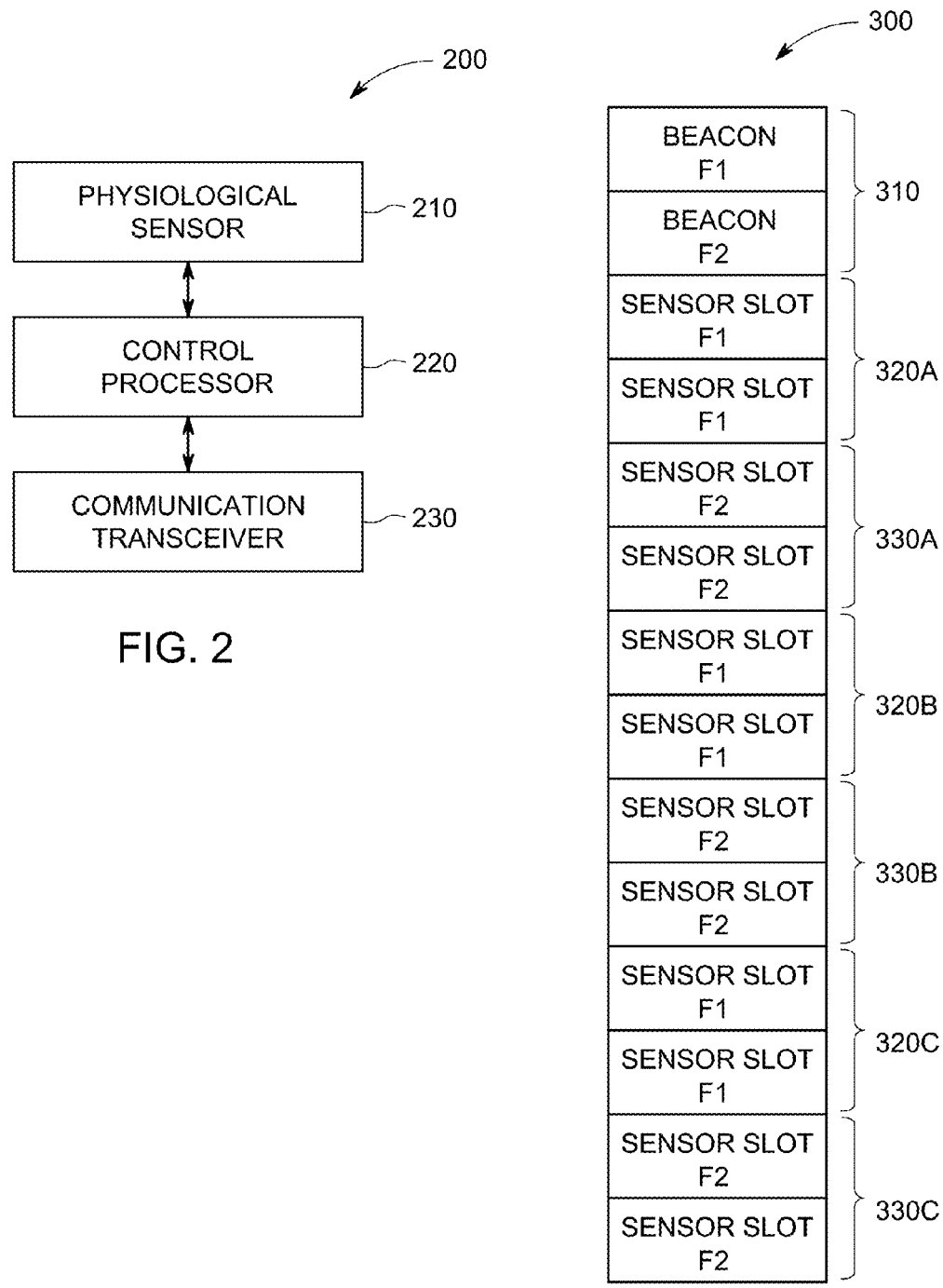

SYSTEM AND METHOD FOR ADAPTIVE INTERFERENCE MITIGATION IN WIRELESS SENSOR NETWORK

BACKGROUND

A wireless body area network (WBAN) includes wearable computing devices which are often used to monitor a patient's vital signs (e.g., blood pressure, heart rate, oxygen levels, electrocardiogram (ECG) data, etc.) in a hospital's telemetry ward. A wireless personal area network (WPAN) is a short-range network covering a range of about forty feet. The WPAN can be used as a gateway by the WBAN to reach telemetry stations and/or repeaters, so that the monitors can communicate their information to a centralized location.

Because of the proximity of hospital beds to one another, WBANs operate in close proximity. This close operating proximity can cause interference between the WBANs. Interference can also occur between to sensor devices of the same WBAN. One solution addressing this interference has been to implement a time domain multiple access (TDMA) based protocol to avoid collisions between packets sent by sensor devices that belong to the same WBAN so as to minimize packet loss (and information degradation). The TDMA approach can use a common schedule among WBANs. In some implementations, WBANs can sense the existence of interfering WBANs, and exchange their TDMA schedules to define when a WBAN can transmit without being exposed to interference generated by another WBAN.

Because of the critical nature of the information being transmitted by a patient's WBAN, the data outage specifications can require a transmission success rate of, for example, about 95%. Conventional monitoring networks address interference by retransmitting a data message multiple times to increase the transmission success rate. However, retransmitting data can result in stale data that might exceed a delay requirement.

For patient health monitoring, the issues of data latency and data outage can be extremely problematic. Vital sign monitoring is an important part of patient care since the general or particular health of the patient is determined, in part, through measurement and interpretation of key physiological indicators. Such physiological data, however, is only of use if it is transmitted in a timely and accurate manner. Transmission of such vital sign data must therefore be timely and be transmitted at a high rate of success in order for a WBAN to be beneficial to patient monitoring.

BRIEF DESCRIPTION OF THE DRAWINGS

FIG. 2 depicts a block diagram of a patient sensor device in accordance with some embodiments;

FIG. 3 depicts a communication frame structure in accordance with some embodiments;

DETAILED DESCRIPTION

Systems and method in accordance with embodiments implement dual-frequency adaptive algorithms for overcoming packet losses in the presence of RF interference and provides real time data delivery of data.

Reliable and real time monitoring of the signals from multiple sensors is crucial for many applications of wireless sensor networks, including but not limited to, for example, monitoring of patients' vital signs using the sensors attached to the patient body. Wireless medium in general does not guarantee the reliable data transmission. For instance, the presence of other wireless networks (e.g., Wifi, Bluetooth, Zigbee, etc.), other patients' WBANs, and/or dynamic changes in RF environment causes data losses and communication interruption. These losses and interruptions can severely impact the quality of patient health monitoring.

Strict requirements can be imposed on the amount of data loss that is acceptable over a specified time period, and on the maximum allowable delay that can be tolerated for a given application. The dual-frequency adaptive communication protocol disclosed herein can reduce the risk of data loss and data latency that are critical in healthcare monitoring applications, but this protocol can also be applied to many other monitoring applications as well (e.g., machine monitoring, environment monitoring, etc.). The reduction in the risk of data loss and data latency provided by embodiments can have many technical and commercial advantages.

Figure 1:
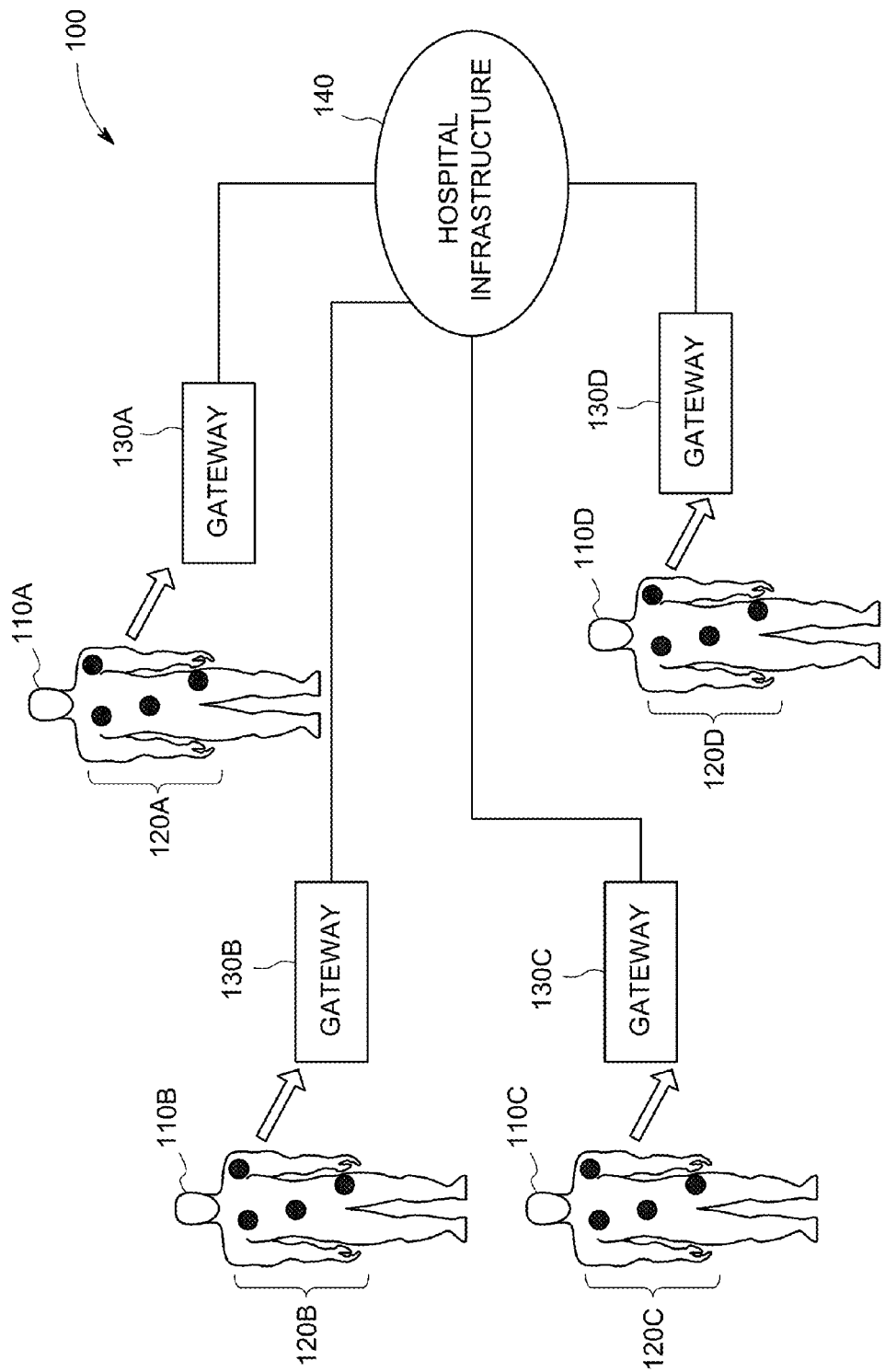
FIG. 1 depicts a multiple-patient monitoring system in accordance with some embodiments.

FIG. 1 depicts multiple-patient monitoring system 100 in accordance with some embodiments, where each patient is equipped with sensor devices connected to a WBAN that transmits the patient's vital functions. FIG. 1 illustrates multiple patients in a hospital ward, where each patient is linked to a WBAN. Each WBAN includes multiple sensors on the patient's body and a gateway device. The gateway device can provide time synchronization signals to the sensor devices for its associated WBAN. The gateway device is connected to the hospital monitoring infrastructure (for example, a bedside monitor and/or nursing station monitors), so the data from the patient can be displayed and interpreted at the monitor. For each patient 110A, 110B, 110C, 110D a respective WBAN 120A, 120B, 120C, 120D can include sensor device(s) and a respective gateway 130A, 130B, 130C, 130D. The WBANs are connected to hospital infrastructure 140, which can include telemetry equipment, alarms, displays, computers, databases, etc.

In accordance with some embodiments, a dual-frequency adaptive protocol (DFAP) can integrate different mechanisms for overcoming packet losses in the presence of RF interference. This DFAP can provide real time data delivery of monitored information (e.g., medical data) from the sensor(s). The DFAP is a time domain multiple access (TDMA) based protocol designed for the synchronous bidirectional transmission of data from sensor devices attached to patient's body to a gateway.

FIG. 2 depicts a block diagram of patient sensor device 200 in accordance with some embodiments. The sensor device can include physiological sensor 210 that monitors a patient's vital sign, control processor 220, and communication transceiver 230. The sensor device can send patient's vital sign data to a respective WBAN (item 120A-D; FIG. 1) for uploading to hospital infrastructure 140 via its respective gateway. In accordance with embodiments, communication transceiver 230 conducts bidirectional communication between sensor device 200 and the gateway. This bidirectional communication can be is organized into frames.

FIG. 3 depicts communication frame structure 300 in accordance with some embodiments. The frame is divided into time periods, called data slots, which have a predetermined, certain duration. In one implementation, beacon slot(s) 310 can be at the beginning of frame. The beacon slots are reserved for the communication from the gateway to the sensor devices. During the beacon slot time period, the gateway sends beacon messages to the sensor devices. These beacon messages are used for synchronization and control of the sensor devices. In accordance with embodiments, each beacon can be sent on a different frequency (for example, there are two beacon messages, one at frequency F1 and another at frequency F2). Each sensor device of a WBAN can listen for the beacon message(s) sent during the beacon slot period. In accordance with some implementation, each beacon message can contain information for every sensor device.

The beacon messages can be sent on different frequencies—e.g., frequencies F1, F2. Data slots 320A-C, 330A-C can be used for data transmissions from the sensor devices back to the gateway. For example, data slot 320A includes two sensor slots that can be transmitted at a predetermined frequency F1. The information in each of these sensor slots can be from different sensor devices (e.g., monitors), or from the same sensor device but with different data (e.g., blood pressure and pulse rate information from an arterial pressure cuff). In some implementations, the information in the sensor slots can be the same data from the same sensor device, which is sent redundantly on two different frequencies to increase the probability of receiving at least one of these packets successfully.

In accordance with other implementations, the number of data slots, their duration, and the number of frequencies can be different from the structure depicted in FIG. 3. Additionally, the duration of data slots for different sensor devices can vary. Data from the sensor devices can be sent twice, at two different frequencies so as to minimize the chance of lost data from interference caused by other WBANs operating in close proximity.

Figure 4:
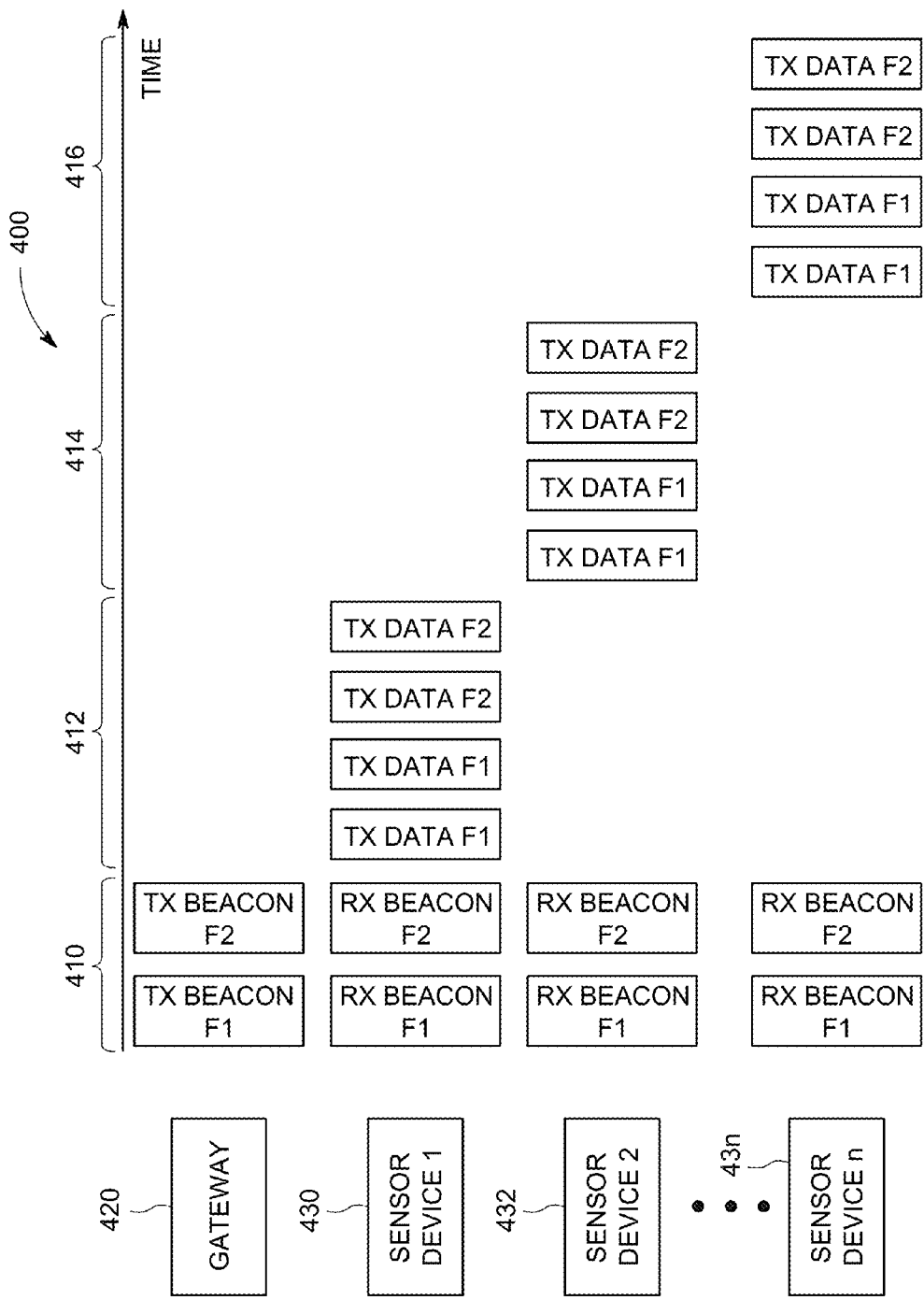
FIG. 4 depicts a timing diagram of synchronized transmissions of data from sensors of the same WBAN in accordance with some embodiments.

FIG. 4 depicts timing diagram 400 of synchronized transmissions of data from sensors of the same WBAN illustrating that data from sensor devices is sent in different time slots in accordance with some embodiments. The data sent in one slot can be interleaved—for example, in one implementation one data packet can contain the data readings from one or more sensor device(s) collected over the last two, or more, frames. In accordance with some embodiments, one data packet sent in one slot can contain both current data and previous data from the same sensor device. So that the previous data reading and the current data reading are interleaved in one packet. One packet cannot contain data from two sensor devices. In addition to interleaving, frequency agility and/or diversity can be used to send the data packets on multiple frequency channels.

In this way, one sensor's reading is being sent multiple times, and at multiple frequencies to the gateway, which increases the probability of this data being received correctly at the gateway. FIG. 4 depicts the timing of a communication frame structure with multiple time slots 410, 412, 414, 416. In the first time slot 410, beacon packets are sent from gateway 420 to sensor devices 430, 432, . . . , 43n of a patient's WBAN.

The beacon packets are sent at the beginning of the communication frame to each sensor device in the patient's WBAN. The beacon packets inform the sensor devices as to which frequencies are to be used for data transmission. During the following time slots, the sensor devices send their sensor readings in an assigned time slot. In accordance with some implementations, each sensor device transmits its data packets two times, each at different frequencies F1 and F2. For example, time slot 412 includes readings from sensor device 430 transmitted twice at frequencies F1, F2; sensor device 432 transmits its data twice during time slot 414; and so on for each sensor device through to sensor device 43n. In accordance with embodiments, not each sensor device of a patient's WBAN need send data in every communication frame.

However, embodiments are not limited to transmissions at two times on two frequencies. The data can be transmitted two or more times at two or more different frequencies. The limiting factors for this implementation are the inherent delay (since one data is sent multiple times) and increased packet traffic (which can increase the packet collisions/interference further).

The frequency agility mechanism is used to change the frequency channels in subsequent frames. The gateway can send beacon messages to the WBAN sensor devices to inform them about the frequencies to use to send packets in the following frame. For each frequency channel F1, F2 a different frequency agility channel pattern is generated. The agility pattern can be generated by each gateway, where the gateway includes two unique frequency agility sequences (for F1 and F2). These frequency agility patterns can be generated in pseudo random fashion. The beacon message at the beginning of each frame contains the information about the frequency that is to be used for communication.

The channels within each agility pattern are generated so that adjacent channels in a pattern are separated by a predetermined frequency offset. The frequency offset can be determined by the communication transceiver 230 within the sensor device based on its internal receiver's filter characteristic (e.g., selectivity response and other radio specifications). The radio selectivity response characteristic informs on the minimum difference in signal strength between a desired signal at some frequency Fa (from sensor device in this WBAN) and the interfering signal at some frequency Fb (from another interfering WBAN) at the receiver, so that the desired signal still can be received correctly. If the network experiences a packet loss at one frequency due to the interference/collision with another network, then after switching to another frequency (which is separated by the frequency offset from the previous) there is less chance for interference. For the same reasons the concurrent channels in F1 and F2 patterns can also be separated by the same frequency offset.

Having frequency channels separated by a predetermined frequency offset increases the chance of a transmitted packet being received correctly. For example, if a packet from one WBAN sent using one frequency is lost due to collision with some other packet from a different WBAN, then other packets sent from the same sensor in another time slot can be sent using a frequency that is further from the frequency at which a packet loss is experienced, in order to increase the chance of the second packet being received correctly.

In accordance with some embodiments, the first and second frequency channels can be selected adaptively. Initially, the sensor nodes transmit their data using the frequency agility sequences for the first and second frequency channel. The gateway receives the data packets from the sensor devices and records the number of lost packets from sensor devices at each frequency channel. Because the gateway expects packets from each sensor device in a certain time slot. If the gateway does not receive a packet from the sensor within some data slot that is reserved exclusively for that sensor it will assume that the packet is lost. If the number of lost packets for the first or second frequency channels is greater that a threshold value, the gateway initiates the frequency change on the channel that experiences the packet losses.

In some implementations, the packets can have header information placed at the beginning of the packet. The header information can include information regarding the packet originator, WBAN identification, data collection time, and other details regarding the system, patient, and data.

The gateway sends the beacon message at the beginning of the next frame to inform one or more sensor devices to change the frequency of one and/or both frequency channels by hopping to the next channel of the frequency agility pattern. After receiving the beacon message from the gateway, the sensor devices switch their first or/and second frequency channel to a new frequency or a new set of frequencies.

In accordance with some embodiments, the first and the second frequency channel can be used to in different ways. The first frequency channel can be used for the bidirectional communication with the gateway using the frequency agility mechanism. One or more sensors use the same frequency from the frequency agility pattern until they receive a beacon message from the gateway with the instruction to change the frequency. The second channel can be used to perform continuous frequency agility, by changing the frequency at each frame.

In this implementation the gateway records the packet losses at the second channel. Additionally, the gateway can track other quality indicators of the received signal for each frequency used by the second frequency channel (e.g., received signal strength indicator (RSSI)). From this information, the gateway can rank the frequency channels based on their quality—e.g., one metric of rank can combine packet error rate and RSSI for each frequency channel. Frequencies at which no packet loss is observed and links have high quality indicators would have a higher metric ranking. The frequency ranking can also include predictive models, which can be based on the current channel statistics (e.g. number lost packets, RSSI, etc.). The predictive model can provide the expected performance of each frequency channel, such as the expected probability of the data loss at each channel.

This frequency ranking can be used in the following way: if the gateway records the packet losses on the first frequency channel, the gateway instructs one or more sensor devices to change the frequency of the first frequency channel. The new frequency used as the first frequency channel is selected as the highest ranked frequency among one or more frequencies which are used by the second frequency channel. Also, a new frequency for the first frequency channel can be selected probabilistically, by giving the higher probability of selection to those frequency channel that are ranked higher.

Figure 5:
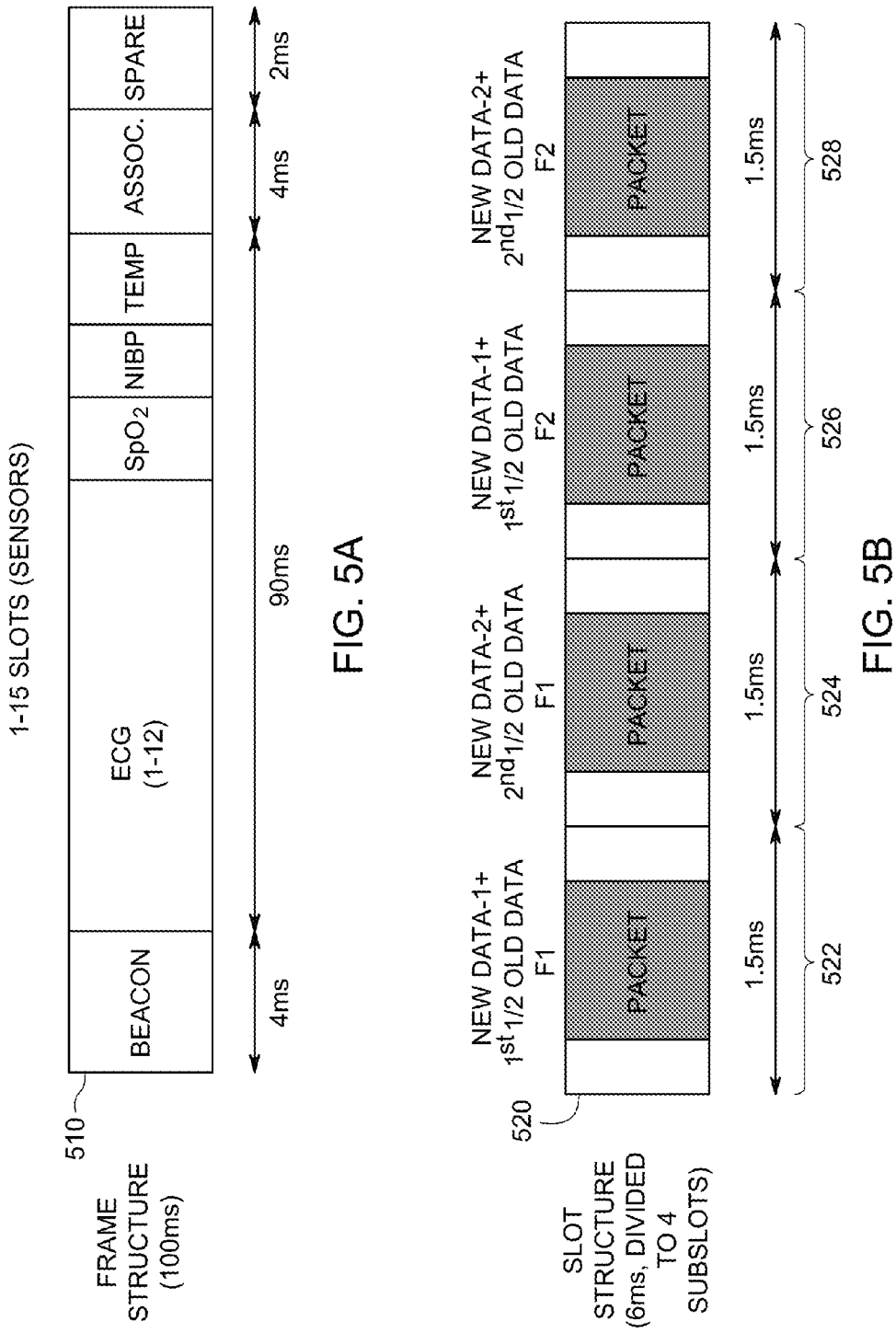
FIG. 5A depicts a communication frame structure in accordance with some embodiments.
FIG. 5B depicts time slot structures of the communication frame structure depicted in FIG. 5A in accordance with some embodiments.

FIG. 5A depicts communication frame structure 510 in accordance with some embodiments. In the depicted implementation, communication frame structure 510 is 100 msec in duration and includes a 4 msec beacon time slot, 6 msec time slots for 15 sensor devices (e.g., electrocardiogram (slots 1-12), blood oxygen, noninvasive blood pressure, and temperature), an association time slot for pairing devices to the gateway, and a spare slot of 2 msec.

FIG. 5B depicts time slot structure 520 for communication frame 510 in accordance with some embodiments. Time slot structure 520 is 6 msec in duration, and is itself divided into four sub-slots 522, 524, 526, 528, where each sub-slot is 1.5 msec. During each sub-slot, a portion of new data along with a portion of old data is transmitted by the sensor device. Under this scheme, one piece of data is transmitted for a total of six times in eight packets over two frames. This scheme provides a higher rate of data integrity, where one measurement is lost if all eight packets are lost.

For example, two possible scenarios for data loss can be (1) an increase in path loss between the gateway and the WBAN nodes; and/or (2) wireless interference from different sources and/or devices. Possible reasons for the first scenario (i.e., path loss increases), can include distance, fading/multipath, body posture of the patient, etc. To determine if data is being lost for these reasons, parameters to be measured include an increase in PER, a decrease in RSSI, and if the transmit power is less than the maximum transmit power. These changes can be overcome by increasing the transmit power of all the sensor devices if all the sensor devices are measured to have an increased path loss; or increase the transmit power for one sensor if that one sensor is having an increased path loss; and/or if all the sensors are at maximum transmit power and there is still an unacceptable path loss, change the frequency.

If there is wireless interference from different sources and/or devices, possible causes can be interference from other patients' WBAN in close proximity, interference from other wireless sources/devices such as WiFi, Zigbee, Bluetooth, etc., interference from an unknown jammer (video game, mobile phone or other device). Wireless interference can be determined if there is an increase in PER along with a mostly unchanged RSSI. If the source of interference is other patients' WBAN and/or unknown jammer(s), multiple sensors can be affected so the frequency could be changed. If the source of interference is other wireless sources, just a few sensors might be affected, so increase the transmit power and then change the frequency.

Figure 6:
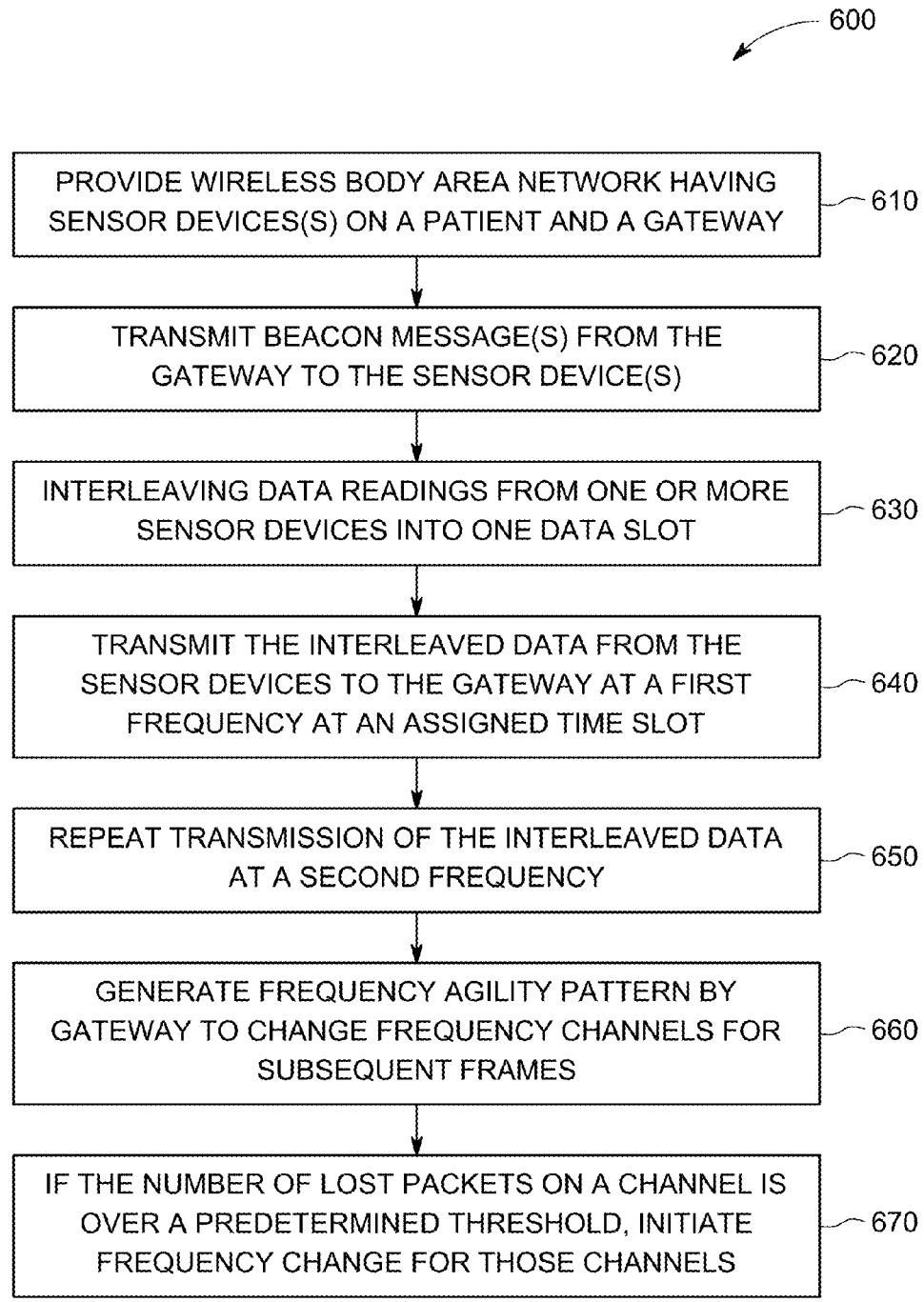
FIG. 6 depicts a process in accordance with some embodiments.

FIG. 6 depicts process 600 for implementing dual-frequency adaptive algorithms for overcoming packet losses in accordance with some embodiments. At step 610, a WBAN including one or more sensor devices and a gateway is provided. At the beginning of a communication frame the gateway transmits, step 620, beacon messages to the sensor devices. Data from one or more sensor devices can be interleaved, step 630, into one data slot. The interleaved data is transmitted, step 640, from the sensor device(s) to the gateway at a first frequency and at an assigned time. Then the interleaved data is transmitted again, step 650, but at a second frequency at the assigned time. The gateway can generate, step 660, a frequency agility pattern to change frequencies for subsequent frame(s). If the number of lost packets (i.e., packets not received at the gateway) on a channel is greater than a predetermined threshold, then a frequency change is initiated for those channels via instruction from the gateway, step 660.

In accordance with an embodiment, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as a method for implementing dual-frequency adaptive algorithms for overcoming packet losses in the presence of RF interference to provide real time data delivery of data.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

The invention claimed is:

1. A system comprising:
    at least two wireless sensor devices positioned to monitor a physiological data of a patient;
    a gateway device in communication with the at least two wireless sensor devices, the at least two wireless sensor devices and the gateway device forming a wireless body area network;
    the gateway device configured to provide time synchronization signals to the at least two wireless sensor devices, the time synchronization signals adhering to a dual-frequency adaptive protocol, wherein the gateway device ranks frequency channels based on quality, wherein the rank includes a predictive model that provides an expected performance of each frequency channel;
    the time synchronization signals including a communication frame structure having a plurality of time slots including two beacon signal time slots and a plurality of data slots;
    each of the at least two wireless sensor devices configured to transmit respective patient data a first time interleaved within a same first one of the plurality of data slots; and
    each of the at least two wireless sensor devices configured to transmit respective patient data a second time interleaved within a same second one of the plurality of data slots;
    wherein a frequency offset is determined by a communication transceiver within the wireless sensor devices as based on a selectivity response characteristic of an internal receiver, the selectivity response characteristic providing a minimum difference in signal strength between a desired signal at a frequency Fa within a wireless body area network (WBAN) and an interfering signal at a frequency Fb from an interfering WBAN at the internal receiver.

2. The system of claim 1, the gateway device configured to communicate patient data received from the at least two wireless sensor devices to a monitoring infrastructure.

3. The system of claim 1, wherein the two beacon signal time slots are at the beginning of the communication frame structure.

4. The system of claim 1, including the gateway device configured to transmit two beacon signals each at a different frequency.

5. The system of claim 1, wherein the first interleaved data transmission and the second interleaved data transmission are each transmitted at respective different frequencies.

6. The system of claim 5, wherein the respective different frequencies are provided to the at least two wireless sensor devices in the beacon signals received from the gateway device.

7. The system of claim 1, wherein the first interleaved data transmission includes both current data and previous data from the at least two wireless sensor devices.

8. The system of claim 1, wherein the beacon signals include a frequency agility pattern that separates adjacent channels by a respective predetermined frequency offset, wherein the wireless sensor devices uses a frequency from the frequency agility pattern until a beacon message is received from the gateway device with instruction to change the frequency.

9. The system of claim 8, each of the at least two wireless sensor devices including a communication transceiver having a filter, and configured to determine the respective predetermined frequency offset based on radio selectivity response characteristics of its filter.

10. The system of claim 1, wherein the predictive model is based on a plurality of current channel statistics.

11. A method comprising:
    providing at least two wireless sensor devices positioned to monitor a physiological data of a patient, and a gateway device in communication with the at least two wireless sensor devices, the at least two wireless sensor devices and the gateway device forming a wireless body area network;
    the gateway device providing time synchronization signals to the at least two wireless sensor devices, the time synchronization signals adhering to a dual-frequency adaptive protocol including a communication frame structure having two beacon signal time slots and a plurality of data slots, wherein the gateway device ranks frequency channels based on quality, wherein the rank includes a predictive model that provides an expected performance of each frequency channel;
    transmitting respective patient data from the at least two wireless sensor devices a first time interleaved within a same first one of the plurality of data slots and then transmitting respective patient data a second time interleaved within a same second one of the plurality of data slots;
    the gateway device determining a frequency agility pattern for subsequent data transmission by comparing a number of lost packets of a channel with a predetermined threshold; and
    initiating a transmission frequency change for the channels where the predetermined threshold is exceeded.

12. The method of claim 11 including the step of communicating patient data received from the at least two wireless sensor devices to a monitoring infrastructure.

13. The method of claim 11 including the step of providing the two beacon signal time slots at the beginning of the communication frame structure.

14. The method of claim 11 including the step of transmitting the two beacon signals each at a different frequency.

15. The method of claim 11 including:
    providing respective different frequencies to the at least two wireless sensor devices in the beacon signals; and
    transmitting the first interleaved data transmission and the second interleaved data transmission at the respective different frequencies.

16. The method of claim 11 including transmitting both current data and previous data from the at least two wireless sensor devices in the first interleaved data transmission.

17. The method of claim 11, separating adjacent channels by a respective predetermined frequency offset.

18. The method of claim 11, wherein the predictive model is based on a plurality of current channel statistics.

19. A non-transitory computer readable medium having stored thereon instructions which when executed by a processor cause the processor to perform a method comprising:
provided at least two wireless sensor devices positioned to monitor a physiological data of a patient, and a gateway device in communication with the at least two wireless sensor devices, the at least two wireless sensor devices and the gateway device forming a wireless body area network;
providing time synchronization signals to the at least two wireless sensor devices, the time synchronization signals adhering to a dual-frequency adaptive protocol including a communication frame structure having two beacon signal time slots and a plurality of data slots;
transmitting respective patient data from the at least two wireless sensor devices a first time interleaved within a same first one of the plurality of data slots and then transmitting respective patient data a second time interleaved within a same second one of the plurality of data slots;
determining a frequency agility pattern for subsequent data transmission by comparing a number of lost packets of a channel with a predetermined threshold; and
initiating a transmission frequency change for the channels where the predetermined threshold is exceeded, wherein a gateway device ranks frequency channels based on quality, wherein the rank includes a predictive model that provides an expected performance of each frequency channel.

20. The medium of claim 19 including instructions that cause the processor to transmit the two beacon signals each at a different frequency.

21. The medium of claim 19 including instructions that cause the processor to:
provide respective different frequencies to the at least two wireless sensor devices in the beacon signals; and
transmit the first interleaved data transmission and the second interleaved data transmission at the respective different frequencies.

22. The medium of claim 19 including instructions that cause the processor to separate adjacent channels by a respective predetermined frequency offset.

23. The medium of claim 19, wherein the predictive model is based on a plurality of current channel statistics.

* * * * *